(12) United States Patent
Cho et al.

(10) Patent No.: US 8,974,393 B2
(45) Date of Patent: Mar. 10, 2015

(54) ULTRASONIC PROBE

(71) Applicant: Samsung Electronics Co., Ltd., Suwon-si (KR)

(72) Inventors: Kyung Il Cho, Seoul (KR); Seung Heun Lee, Seoul (KR); Bae Hyung Kim, Seoul (KR); Young Il Kim, Suwon-si (KR); Jong Keun Song, Yongin-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 64 days.

(21) Appl. No.: 13/873,342

(22) Filed: Apr. 30, 2013

(65) Prior Publication Data

US 2013/0286593 A1 Oct. 31, 2013

(30) Foreign Application Priority Data

Apr. 30, 2012 (KR) ........................ 10-2012-0045336

(51) Int. Cl.
*A61B 8/00* (2006.01)
*G01N 29/24* (2006.01)
*H05K 1/02* (2006.01)
*G01N 29/32* (2006.01)
*H05K 7/20* (2006.01)
*B06B 1/02* (2006.01)

(52) U.S. Cl.
CPC ........ *H05K 7/20336* (2013.01); *G01N 29/2406* (2013.01); *H05K 2201/09072* (2013.01); *H05K 2201/064* (2013.01); *H05K 1/0204* (2013.01); *G01N 29/326* (2013.01); *H05K 2201/10598* (2013.01); *B06B 1/0292* (2013.01)
USPC ............ 600/459; 600/437; 600/407; 600/441

(58) Field of Classification Search
USPC .......................... 600/437, 407, 441, 443, 459
See application file for complete search history.

(56) References Cited

U.S. PATENT DOCUMENTS

| | | | |
|---|---|---|---|
| 5,043,845 | A | 8/1991 | McDermott et al. |
| 5,272,599 | A | 12/1993 | Koenen |

(Continued)

FOREIGN PATENT DOCUMENTS

| | | |
|---|---|---|
| DE | 19806801 A1 | 9/1999 |
| DE | 20204266 U1 | 8/2002 |

(Continued)

OTHER PUBLICATIONS

Communication, dated Jul. 4, 2013, issued by the Korean Patent Office in counterpart Korean Application No. 10-2012-0045336.
Communication, dated Jul. 22, 2013, issued by the European Patent Office in counterpart European Application No. 13166063.1.

*Primary Examiner* — Joel Lamprecht
(74) *Attorney, Agent, or Firm* — Sughrue Mion, PLLC

(57) ABSTRACT

An ultrasonic probe, from which heat generated in an integrated circuit which is bonded to a cMUT is released, is provided. The ultrasonic probe includes a transducer which is configured to generate ultrasound radiation, an integrated circuit which is installed on the rear surface of the transducer, a printed circuit board which is installed on the rear surface of the integrated circuit and has an opening via which the rear surface of the integrated circuit is at least partially exposed, a heat spreader which has a protrusion inserted into the opening of the printed circuit board and is configured to absorb heat generated in the integrated circuit, and a heat dissipation module which is configured to release heat absorbed by the heat spreader to the outside.

16 Claims, 14 Drawing Sheets

(56) References Cited

U.S. PATENT DOCUMENTS

| | | |
|---|---|---|
| 5,560,362 A | 10/1996 | Sliwa, Jr. et al. |
| 8,544,330 B2 * | 10/2013 | Oaks et al. ............... 73/632 |
| 2005/0152118 A1 | 7/2005 | Cho |
| 2008/0188755 A1 | 8/2008 | Hart |
| 2008/0253090 A1 | 10/2008 | Janisch et al. |
| 2009/0207568 A1 | 8/2009 | Haveri |

FOREIGN PATENT DOCUMENTS

| | | |
|---|---|---|
| JP | 2007-209699 A | 8/2007 |
| JP | 2008-079700 A | 4/2008 |
| JP | 2010-193973 A | 9/2010 |
| JP | 2011-004874 A | 1/2011 |

* cited by examiner

ULTRASONIC PROBE

CROSS-REFERENCE TO RELATED APPLICATION

This application claims priority from Korean Patent Application No. 10-2012-0045336, filed on Apr. 30, 2012 in the Korean Intellectual Property Office, the disclosure of which is incorporated herein by reference in its entirety.

BACKGROUND

1. Field

Embodiments relate to an ultrasonic probe which uses a capacitive micromachined ultrasonic transducer (cMUT).

2. Description of the Related Art

An ultrasonic diagnosis apparatus irradiates ultrasound toward a target region of the interior of a body of an object from the surface of the object, and non-invasively acquires an image which relates to soft tissue tomograms or a blood stream by receiving a reflected ultrasonic signal (i.e., an ultrasonic echo signal).

The ultrasonic diagnosis apparatus is small and inexpensive, executes display in real time and has high safety without radiation exposure, as compared to other image diagnosis apparatuses, such as an X-ray diagnosis apparatus, an X-ray computerized tomography (CT) scanner, a magnetic resonance imager (MRI), and a nuclear medicine diagnosis apparatus, and is thus widely used for heart diagnosis, celiac diagnosis, urinary diagnosis, and obstetrical diagnosis.

The ultrasonic diagnosis apparatus includes an ultrasonic probe which transmits an ultrasonic signal toward an object and receives an ultrasonic echo signal which is reflected by the object, which received ultrasonic echo signal may be used to acquire an ultrasonic image of the object.

In general, a piezoelectric material that generates ultrasound by converting electrical energy into mechanical energy is widely used as a transducer generating ultrasound in an ultrasonic probe.

In recent years, a capacitive micromachined ultrasonic transducer (cMUT) has been developed as a new concept in the field of ultrasonic transducers.

The cMUT that is a relatively new concept in the field of ultrasonic transducers which transmit and receive ultrasound by using vibrations of hundreds or thousands of micro-processed thin films is manufactured based on micro electro mechanical system (MEMS) technology. A capacitor is formed by forming a lower electrode and an insulating layer on a semiconductor substrate commonly used in semiconductor manufacturing processes, forming an air gap on the insulating layer including the lower electrode, forming a thin film with a thickness of several to thousands of angstroms on the air gap, and forming an upper electrode on the thin film.

When an alternating current (AC) signal is applied to the capacitor, ultrasonic waves are generated by vibration of the thin film. Conversely, when the thin film is caused to vibrate by external ultrasonic waves, the capacitance of the cMUT varies. By detecting such capacitance variation, ultrasonic waves are detected.

Because one cMUT has a diameter of dozens of micrometers ($\mu m$), an array of tens of thousands of cMUT has a size which is on the order of approximately several millimeters. In addition, because tens of thousands of sensors may be accurately aligned at desired positions via a single semiconductor manufacturing process, and cMUT elements may be bonded to application-specific integrated circuits (ASICs) by chip bonding, such as flip-chip bonding, in order to apply electrical signals to the cMUTs, process complexity due to wiring may be overcome.

These features of the cMUT are suitable for a manufacture of a transducer which has a two-dimensional (2D) array, and may facilitate development of multi-channel transducers.

However, while an amount of heat which is generated in electrical circuits which are designed for driving an ultrasonic probe which includes a relatively small number of transducers is approximately equal to one watt (i.e., 1 W), which may be easily released via a probe case, heat which is generated in electrical circuits which are designed for driving an ultrasonic probe which includes multi-channel transducers is approximately equal to 7 W. Thus, there is a need to develop techniques to dissipate heat from the ultrasonic probe and cool the ultrasonic probe.

SUMMARY

One or more embodiments provide an ultrasonic probe which is configured to absorb heat which is generated in application-specific integrated circuits (ASICs) to which capacitive micromachined ultrasonic transducers (cMUTs) are bonded by using a heat spreader and by releasing heat which is absorbed by the heat spreader to the outside via a heat dissipation module.

Additional aspects of the embodiments will be set forth in part in the description which follows and, in part, will be obvious from the description, or may be learned by practice of the exemplary embodiments.

In accordance with an aspect of an exemplary embodiment, there is provided an ultrasonic probe which includes a transducer which is configured to generate ultrasound irradiation, an integrated circuit which is installed on a rear surface of the transducer, a printed circuit board which is installed on a rear surface of the integrated circuit and which includes an opening via which the rear surface of the integrated circuit is at least partially exposed, a heat spreader which includes a protrusion which is inserted into the opening of the printed circuit board and which is configured to absorb heat which is generated in the integrated circuit, and a heat dissipation module which is configured to release heat which is absorbed by the heat spreader to an outside.

A gap may be provided between the protrusion of the heat spreader and the integrated circuit.

The gap may be filled with at least one of a thermal grease and a phase change material.

The heat dissipation module may include a heat pipe which is configured to transfer heat which is absorbed by the heat spreader in a direction which is opposite to an ultrasound irradiation direction, and a heat sink which is configured to release heat which is transferred by the heat pipe to the outside.

The heat spreader may include an insertion groove into which the heat pipe is insertable, and the heat pipe may be inserted into the insertion groove.

The insertion groove may extend from the rear surface of the heat spreader toward the protrusion.

The heat sink may include a heat dissipation plate which is configured to disperse heat which is transferred by the heat pipe and a heat dissipation fan which is configured to release heat which is dispersed by the heat dissipation plate to the outside.

A fixing plate may be installed on a rear surface of the heat spreader, and a coupling member may connect the fixing plate to the printed circuit board such that the heat spreader is fixed to the printed circuit board.

The transducer may include a capacitive micromachined ultrasonic transducer (cMUT).

In accordance with an aspect of another exemplary embodiment, there is provided an ultrasonic probe which includes a transducer which is configured to generate ultrasound irradiation, an integrated circuit which is installed on a rear surface of the transducer, a printed circuit board which is installed on a rear surface of the integrated circuit and which includes an opening via which the rear surface of the integrated circuit is at least partially exposed, and a heat spreader which is configured to absorb heat which is generated in the integrated circuit via the opening of the printed circuit board.

The heat spreader may be installed on a rear surface of the printed circuit board, and a space between a portion of the rear surface of the integrated circuit which is exposed via the opening and a portion of a the front surface of the heat spreader which corresponds to the opening may be filled with a thermal medium.

The thermal medium may include at least one of a thermal grease and a phase change material.

A fixing plate may be installed on a rear surface of the heat spreader, and a coupling member may connect the fixing plate to the printed circuit board such that the heat spreader is fixed to the printed circuit board.

The ultrasonic probe may further include a heat pipe which is configured to transfer heat which is absorbed by the heat spreader in a direction which is opposite to an ultrasound irradiation direction and a heat sink which is configured to release heat which is transferred by the heat pipe to an outside.

The heat spreader may include an insertion groove into which the heat pipe is insertable, and the heat pipe may be inserted into the insertion groove.

The heat sink may include a heat dissipation plate which is configured to disperse heat which is transferred by the heat pipe and a heat dissipation fan which is configured to release heat which is dispersed by the heat dissipation plate to the outside.

In accordance with an aspect of another exemplary embodiment, there is provided an ultrasonic probe which includes a transducer which is configured to generate ultrasound irradiation, an integrated circuit which is installed on a rear surface of the transducer, a printed circuit board which is installed on a rear surface of the integrated circuit and which includes an opening via which the rear surface of the integrated circuit is at least partially exposed, a heat spreader which is disposed at a rear surface of the printed circuit board and which includes a protrusion which is inserted into the opening of the printed circuit board and which is configured to absorb heat which is generated in the integrated circuit, a heat pipe which is configured to transfer heat which is absorbed by the heat spreader in a direction which is opposite to an ultrasound irradiation direction, and a heat sink which is configured to release heat which is transferred by the heat pipe to an outside, wherein the heat spreader includes an insertion groove into which the heat pipe is inserted, and a gap is provided between the protrusion of the heat spreader and the integrated circuit.

BRIEF DESCRIPTION OF THE DRAWINGS

The above and/or other aspects will become apparent and more readily appreciated from the following description of exemplary embodiments, taken in conjunction with the accompanying drawings of which.

DETAILED DESCRIPTION

Figure 1:
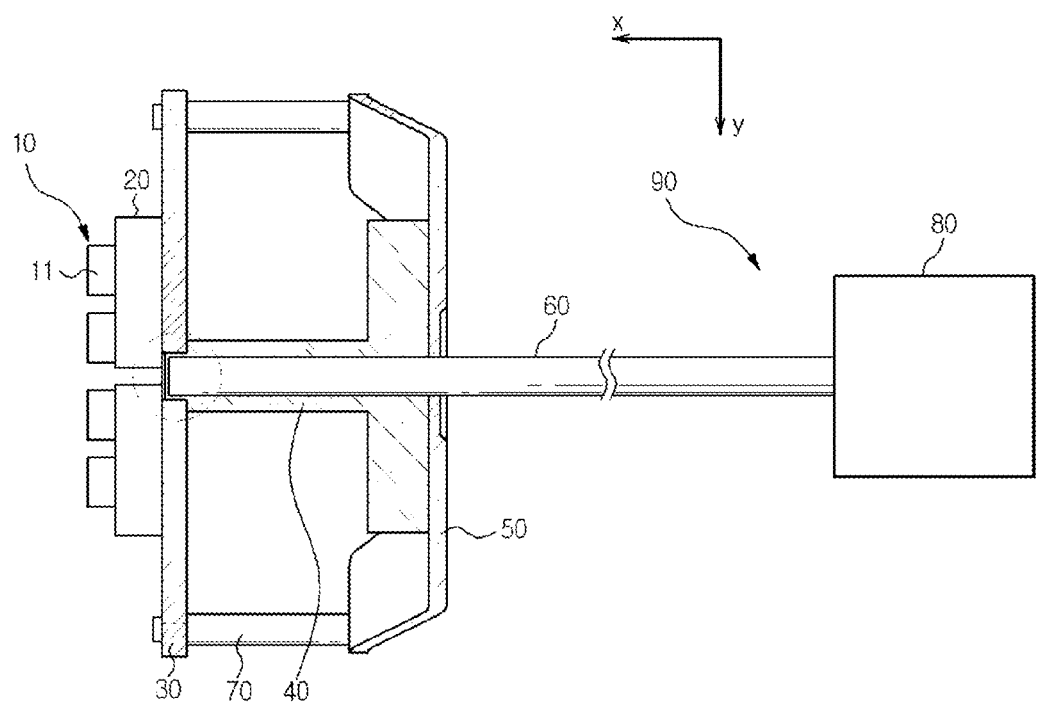
FIG. 1 is a cross-sectional view which illustrates an ultrasonic probe, according to an exemplary embodiment.

Reference will now be made in detail to exemplary embodiments, examples of which are illustrated in the accompanying drawings, wherein like reference numerals refer to like elements throughout.

Figure 2:
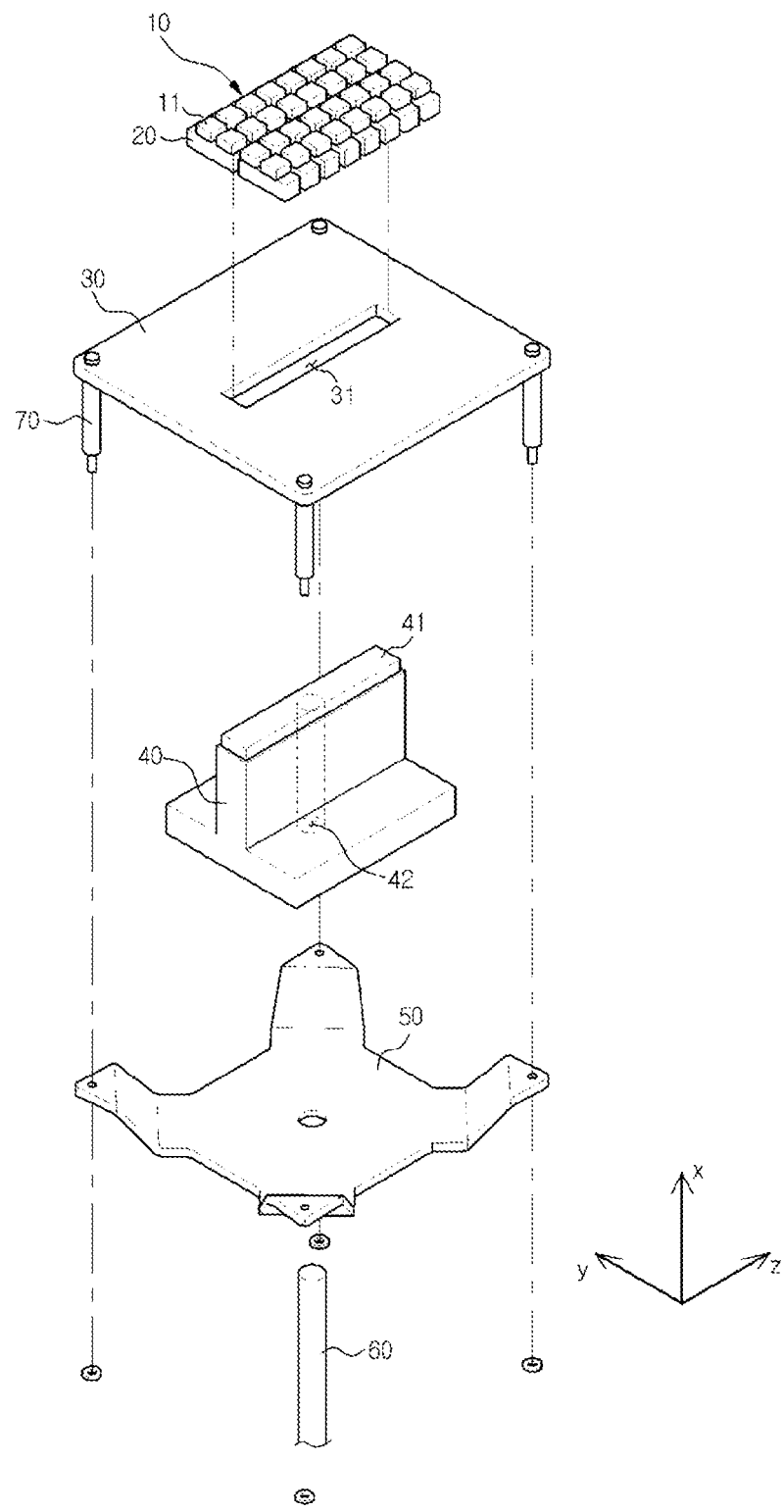
FIG. 2 is an exploded perspective view which illustrates an ultrasonic probe, according to an exemplary embodiment.
Figure 3:
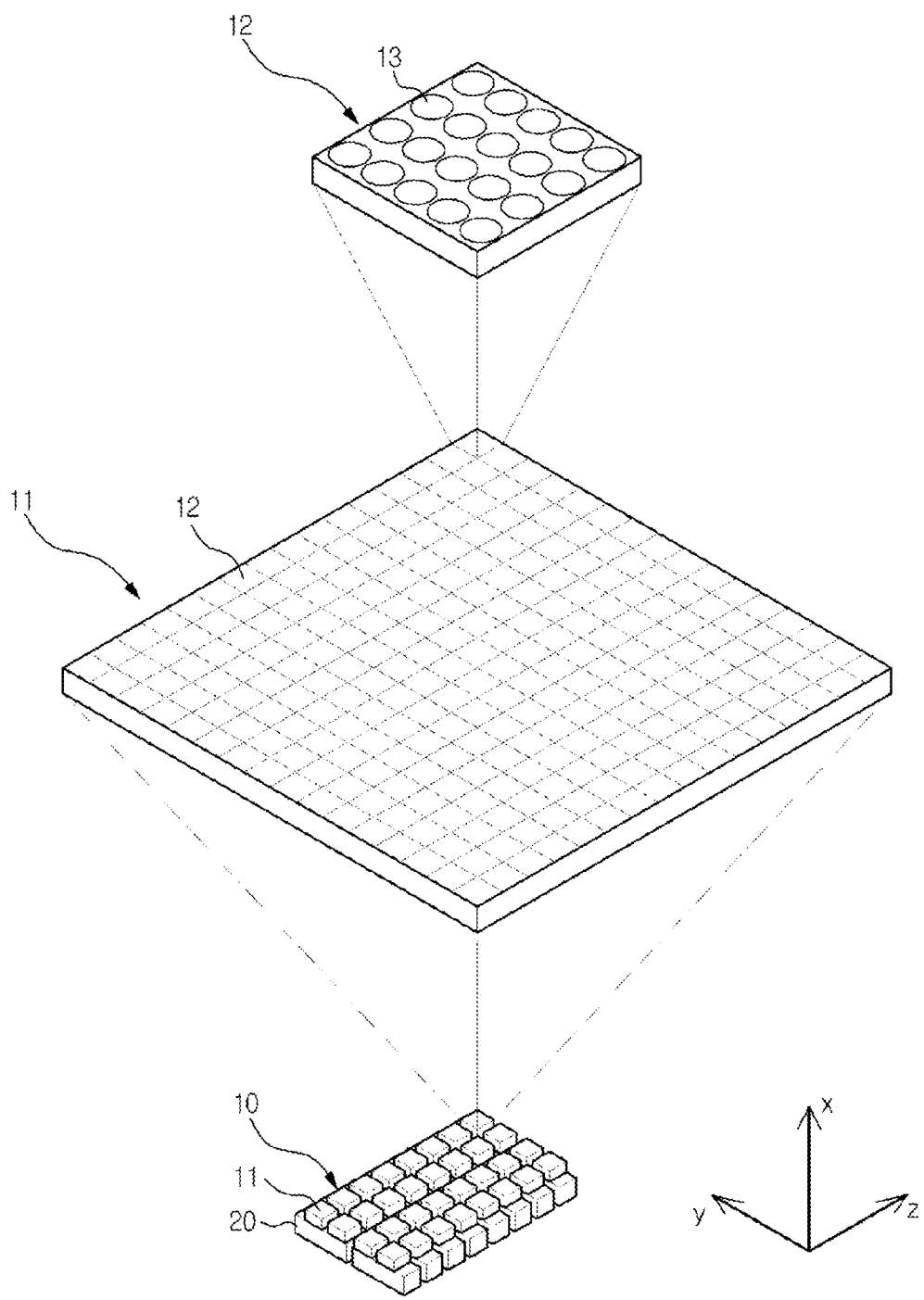
FIG. 3 is a schematic diagram which illustrates a transducer of an ultrasonic probe, according to an exemplary embodiment.
Figure 4:
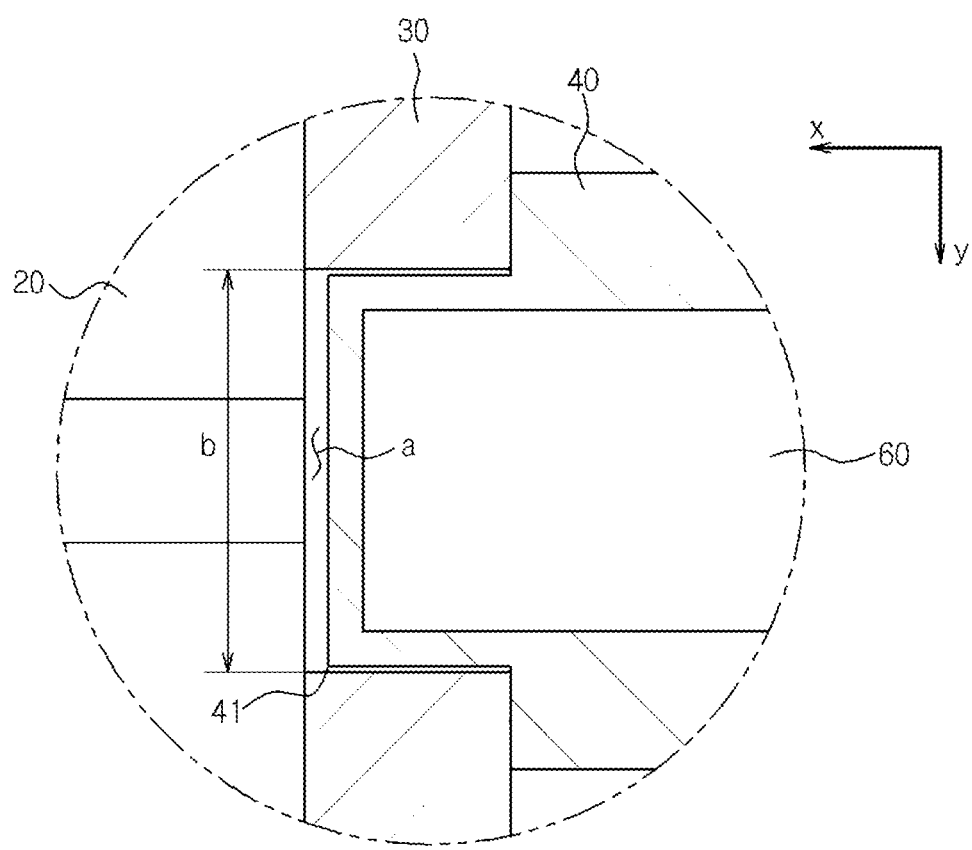
FIG. 4 is a partially enlarged view of FIG. 1.

FIG. 1 is a cross-sectional view which illustrates an ultrasonic probe, according to an exemplary embodiment. FIG. 2 is an exploded perspective view which illustrates an ultrasonic probe, according to an exemplary embodiment. FIG. 3 schematically illustrates a transducer of an ultrasonic probe, according to an exemplary embodiment. FIG. 4 illustrates an enlarged insertion structure of the heat spreader of FIG. 1.

Referring to FIG. 1, the ultrasonic probe according to an exemplary embodiment includes a capacitive micromachined ultrasonic transducer (cMUT) array 10, an integrated circuit 20 which is installed on the rear surface of the cMUT array 10, and a printed circuit board 30 which is installed on the rear surface of the integrated circuit 20.

The cMUT array 10 may be a two-dimensional array, such as is shown in FIGS. 2 and 3.

In particular, a basic unit which constitutes the cMUT array 10 is referred to as a tile 11.

The tile 11 includes elements 12 which are aligned in a two-dimensional array. In one element 12, a plurality of thin films 13, which vibrate in response to an electrical signal applied thereto, is arranged in a two-dimensional array.

FIG. 3 illustrates an enlarged view of a structure of the cMUT array 10.

For example, as shown at the bottom portion of FIG. 3, the cMUT array 10 may have a 4×8 two-dimensional array structure which includes 32 tiles 11.

In addition, as shown at the central portion of FIG. 3, each of the tiles 11 may have a 16×16 two-dimensional array structure which includes 256 elements 12.

For example, as shown at the top portion of FIG. 3, each of the elements 12 may include 20 thin films 13, which vibrate in response to an electrical signal applied thereto in order to generate ultrasonic waves.

In this regard, for example, one cMUT array 10 may include a total of 163,840 thin films 13.

As described above, when the cMUT array 10, which acts as a transducer of the ultrasonic probe, has a 4×8 two-dimensional array structure including 32 tiles 11, two integrated circuits 20 may be respectively bonded to two upper rows of the tiles 11 and two lower rows of the tiles 11 of the cMUT array 10 in order to respectively control two electrical signals which are applied to the two upper rows of the tiles 11 and the two lower rows of the tiles 11.

For example, the cMUT array 10 may be bonded to the integrated circuits 20, such as, for example, application-specific integrated circuits (ASICs), by flip-chip bonding.

The ASICs bonded to the cMUT array 10 may have signal lines which are bonded to the printed circuit board 30 by wire bonding.

When an electrical signal is applied via the printed circuit board 30, an electrical signal which is applied to the cMUT array 10 is controllable based on logics of the ASIC, thereby enabling a control with respect to a generation of ultrasound irradiation.

This alignment of the cMUT array 10 and the integrated circuit 20 is an example, and the alignment thereof may have another shape or structure.

An ultrasonic probe according to an exemplary embodiment has a structure which is suitable for efficient heat dissipation of the ultrasonic probe by efficiently releasing heat generated in the integrated circuit 20 to the outside of the ultrasonic probe.

The structure for heat dissipation includes a heat spreader 40 which absorbs heat which is generated in the integrated circuit 20 and a heat dissipation module 90 which releases heat absorbed by the heat spreader 40.

The heat spreader 40 may be formed of a metal, such as, for example, aluminum.

In order to efficiently transfer heat which is generated in the integrated circuit 20 to the heat spreader 40, an opening 31 is formed at the printed circuit board 30 of the ultrasonic probe, as shown in FIG. 2, such that the heat spreader 40 and the integrated circuit 20 thermally contact each other.

In particular, as shown in FIG. 2, the opening 31 is formed at the printed circuit board 30, which is bonded to the rear surface of the integrated circuit 20, such that the rear surface of the integrated circuit 20 is partially exposed, and the heat spreader 40 has a protrusion 41 which is inserted into the opening 31 of the printed circuit board 30.

The protrusion 41 of the heat spreader 40 is inserted into the opening 31 of the printed circuit board 30 in order to thermally contact the integrated circuit 20, thereby absorbing heat which is generated in the integrated circuit 20.

FIG. 4 illustrates an enlarged insertion structure of the protrusion 41 of the heat spreader 40. As shown in FIG. 4, the protrusion 41, which is inserted into the opening 31, does not directly contact the integrated circuit 20, and a gap a is provided therebetween.

In particular, direct contact between the protrusion 41 and the integrated circuit 20 may be prevented by forming a step difference at the protrusion 41 such that the protrusion 41 is inserted to a predetermined depth when the protrusion 41 is inserted into the opening 31.

When the integrated circuit 20 is in direct contact with the heat spreader 40, external mechanical impact may be directly transferred to the integrated circuit 20. Thus, a gap a is formed between the protrusion 41 of the heat spreader 40 and the integrated circuit 20 in order to reduce and/or avoid any effects from external mechanical impacts with respect to the integrated circuit 20.

The gap a may be filled with a thermal medium which has a high thermal conductivity, such as, for example, a thermal grease or a phase change material.

When the gap a is filled with the thermal medium which has a high thermal conductivity, the protrusion 41 of the heat spreader 40 thermally contacts the rear surface of the integrated circuit 20 via the thermal grease or phase change material, which acts as a medium.

Figure 5:
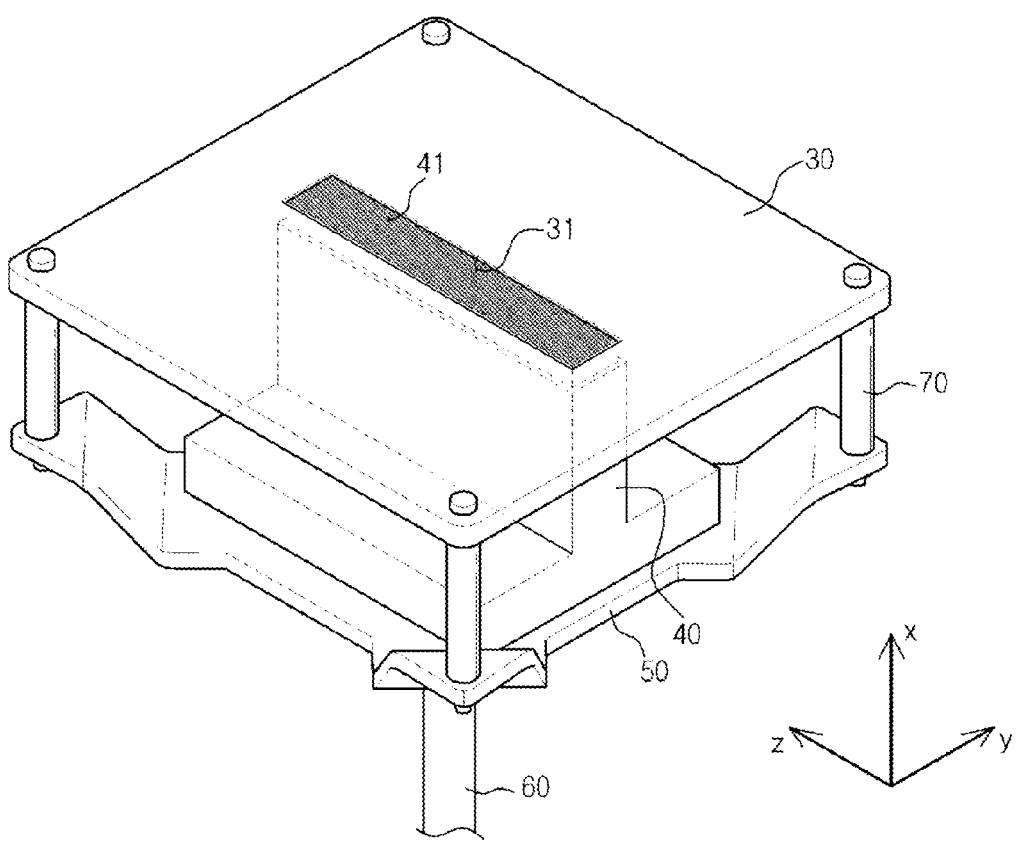
FIGS. 5 and 6 are perspective views which illustrate an ultrasonic probe, according to an exemplary embodiment.

FIG. 5 is a perspective view which illustrates a structure in which the protrusion 41 of the heat spreader 40 is inserted into the opening 31 of the printed circuit board 30.

As shown in FIGS. 2 and 5, the opening 31 may have a rectangular shape which includes a relatively longer width in the z-axis direction and a relatively shorter length in the y-axis direction.

In addition, the opening 31 may be formed at a central region of the printed circuit board 30 such that the protrusion 41 thermally contacts two integrated circuits 20 that are bonded to the front surface of the printed circuit board 30.

A fixing plate 50 is installed on the rear surface of the heat spreader 40 in order to fix the heat spreader 40 to the printed circuit board 30.

Figure 6:
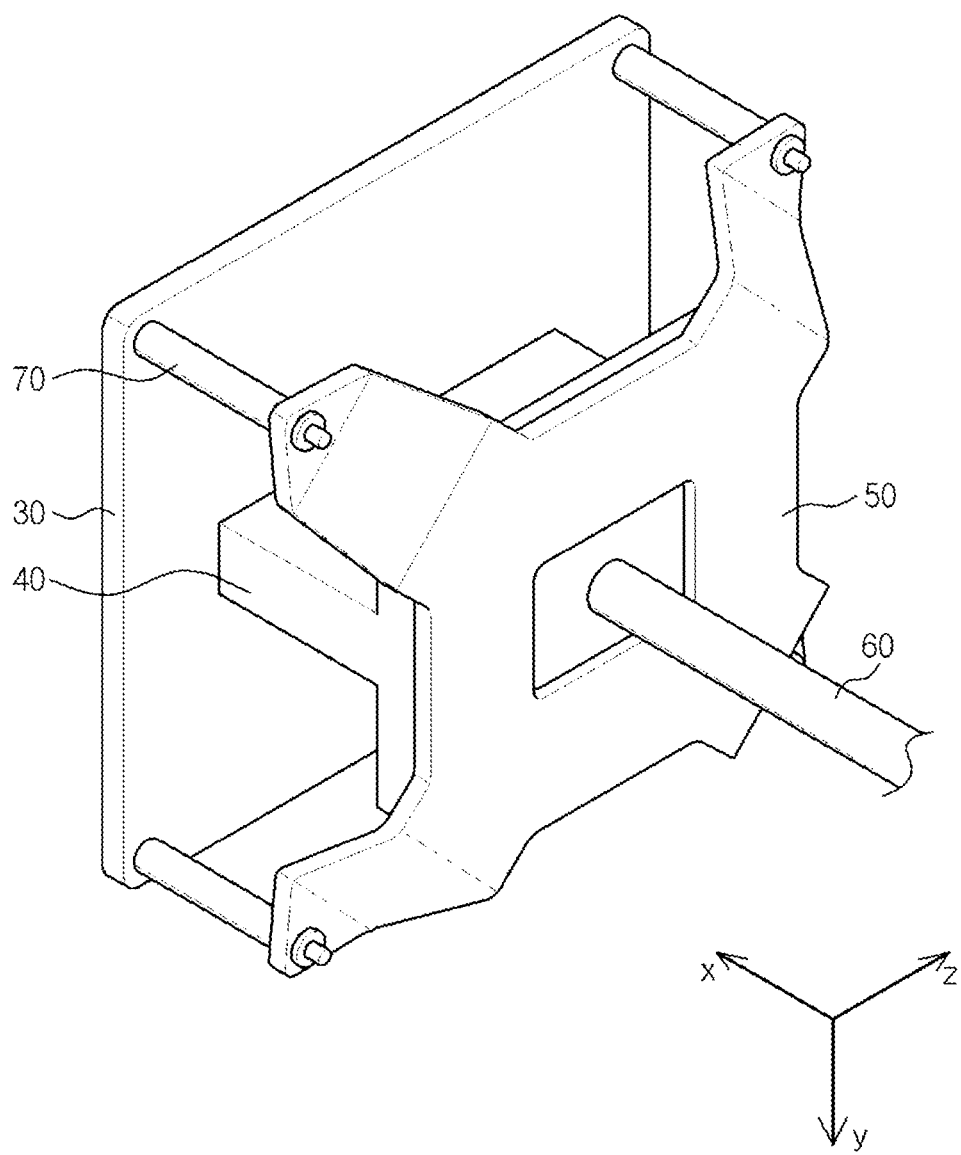

Referring to FIGS. 2 and 6, the fixing plate 50 is installed on the rear surface of the heat spreader 40, and the fixing plate 50 is connected to the printed circuit board 30 by a coupling member 70.

The fixing plate 50, which is installed on the rear surface of the heat spreader 40, is connected to the printed circuit board 30 by the coupling member 70. Thus, the heat spreader 40 is fixed to the printed circuit board 30 by the fixing plate 50.

By fixing the heat spreader 40 to the printed circuit board 30, the gap a may be provided such that the integrated circuit 20 and the protrusion 41 are spaced apart from each other by a uniform distance, and a physical deformation of a connection structure of the heat spreader 40 which might otherwise be caused by an external impact may be prevented.

Heat which is absorbed by the heat spreader 40 is released to the outside of the ultrasonic probe via the heat dissipation module 90. The heat dissipation module 90 includes a heat pipe 60 and a heat sink 80.

Figure 7:
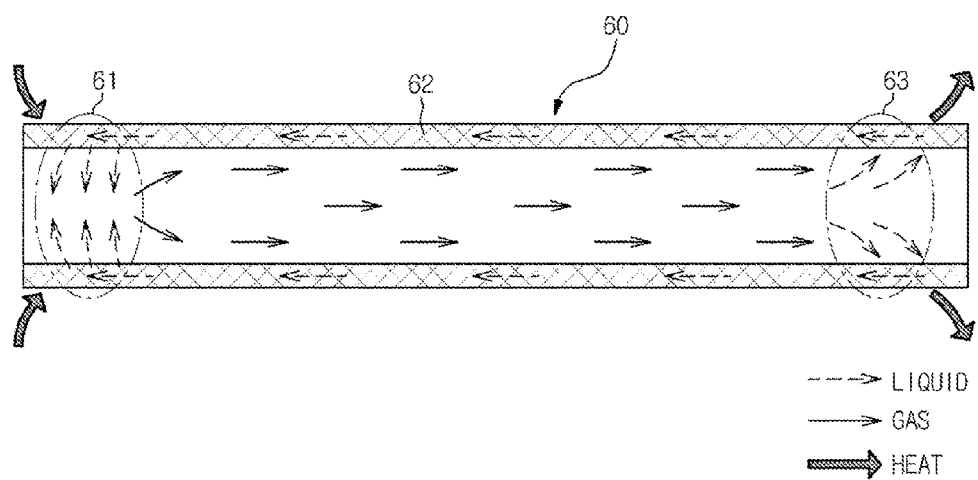
FIG. 7 is a schematic diagram which illustrates a principle of operation of a heat pipe of an ultrasonic probe, according to an exemplary embodiment.

FIG. 7 schematically illustrates a principle of operation of the heat pipe 60.

The heat pipe 60 is a device which is fabricated by injecting a working fluid into a sealed pipe-shaped container and evacuating the container into a vacuum state.

The working fluid is present in two phases in the heat pipe 60, and transfers heat.

Referring to FIG. 7, when heat is applied to an evaporating portion 61 of the heat pipe 60, heat is transferred into the heat pipe 60 by thermal conduction.

In the heat pipe 60, when a high pressure is applied, the working fluid evaporates from the surface of a microstructure (i.e., a wick) 62 at a low temperature.

The evaporation of the working fluid increases gas density and pressure in the evaporating portion 61. Accordingly, a pressure gradient is formed in the central passage of gas in a direction toward the condensing portion 63 in which the gas density and pressure are relatively low, thereby causing the gas to move.

In this regard, the gas moves while carrying a relatively large amount of heat which corresponds to latent heat of evaporation.

Gas which has moved to the condensing portion 63 is condensed at an inner wall of the condensing portion 63, which has a relatively low temperature, and during the condensation process, the gas emits heat and returns to a liquid phase.

The working fluid, which has thereby returned to the liquid phase, then moves to the evaporating portion 61 via internal pores of the microstructure 62 by capillary pressure of the microstructure 62 or gravity.

The transfer of heat is continuously conducted as this process is repeated.

The evaporating portion 61 of the heat pipe 60 contacts the heat spreader 40, and the heat pipe 60 transfers heat which is generated in the integrated circuit 20 to the rear side of the ultrasonic probe, according to the heat transfer process as described above.

As shown in FIG. 2, the heat spreader 40 has an insertion groove 42 into which the heat pipe 60 may be inserted in order to facilitate an efficient transfer of heat to the heat pipe 60.

The heat pipe 60 is inserted into the central region of the rear surface of the heat spreader 40 via the insertion groove 42 of the heat spreader 40, as shown in FIGS. 2 and 6.

The insertion groove 42 may have a sufficient depth to reach the protrusion 41 of the heat spreader 40, as shown in FIG. 2.

By inserting the heat pipe 60 into the protrusion 41 of the heat spreader 40 which is thermally contacting the integrated circuit 20, thermal resistance may be minimized, and heat which is generated in the integrated circuit 20 may be efficiently transferred to the heat pipe 60 via the heat spreader 40.

The length b of the opening 31 of the printed circuit board 30 in the y-axis direction and a width of the protrusion 41 of the heat spreader 40 in the y-axis direction may be determined in consideration of a diameter of the heat pipe 60 and a thermal contact area between the integrated circuit 20 and the protrusion 41 of the heat spreader 40.

Heat which is transferred via the heat pipe 60 is released to the outside of the ultrasonic probe via the heat sink 80, which is provided at the condensing portion 63 of the heat pipe 60.

Figure 8:
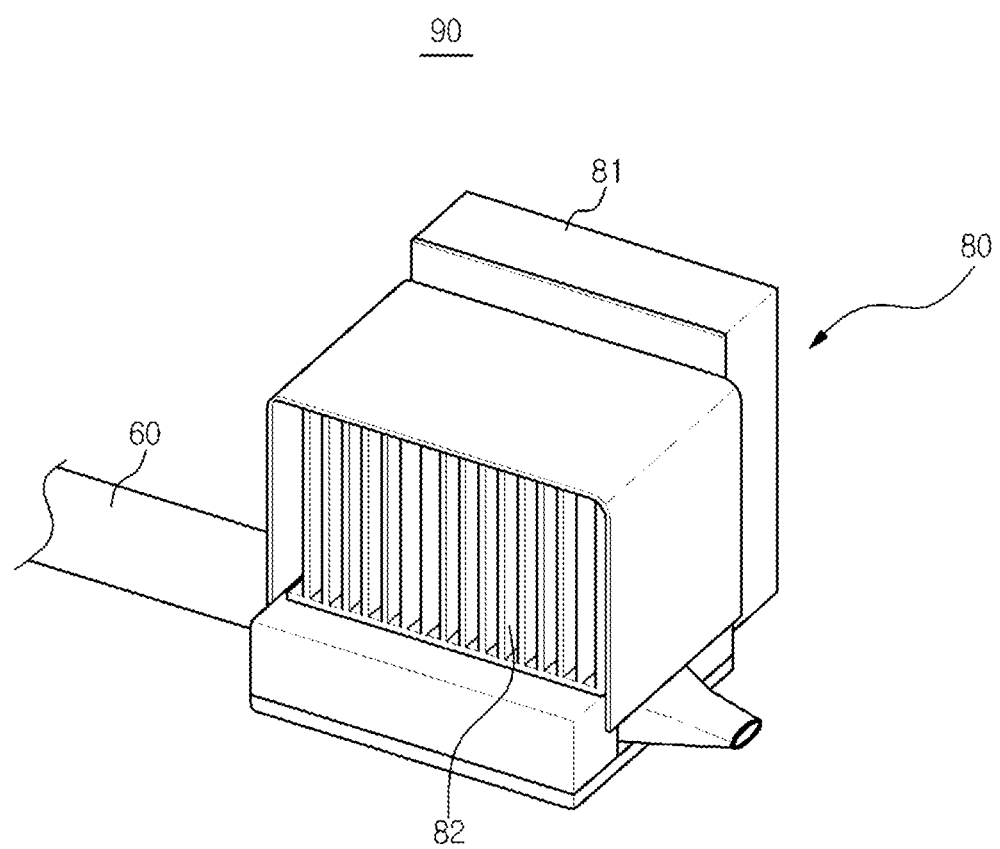
FIG. 8 is a perspective view which illustrates a heat dissipation module of an ultrasonic probe, according to an exemplary embodiment.

Referring to FIG. 8, the heat sink 80 includes a heat dissipation plate 82, which includes a plurality of metal fins which may be formed, for example, of aluminum, and/or of a similar metallic material, in order to disperse heat which is transferred by the heat pipe 60, and a heat dissipation fan 81 which releases the heat which is dispersed by the heat dissipation plate 82 to the outside.

The condensing portion 63 of the heat pipe 60 contacts the heat dissipation plate 82 of the heat sink 80. When the gas which has moved to the condensing portion 63 is condensed at the inner wall of the condensing portion 63, which has a relatively low temperature in order to facilitate a release of heat, the heat dissipation plate 82 disperses the heat which is released by the condensing portion 63 of the heat pipe 60.

Then, heat which is dispersed by the heat dissipation plate 82 is released to the outside of the ultrasonic probe by the heat dissipation fan 81.

Figure 9:
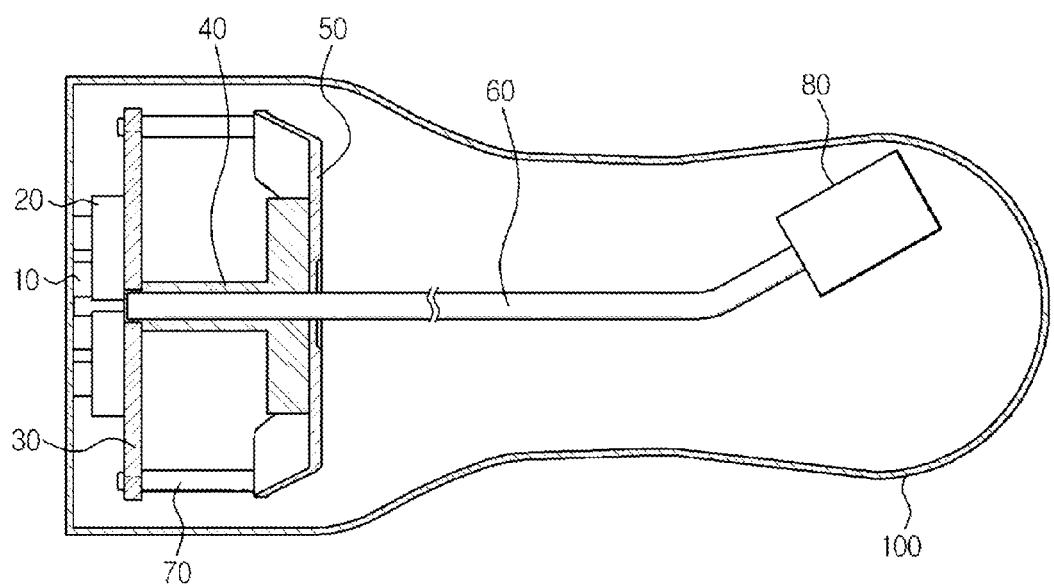
FIG. 9 is a schematic diagram which illustrates the ultrasonic probe of FIG. 1 disposed in a housing.

Referring to FIG. 9, the heat sink 80 is disposed at the rear end of the ultrasonic probe.

In consideration of a physical arrangement of signal lines of the ultrasonic probe, the heat sink 80 may be disposed at the rear end of the ultrasonic probe.

In addition, an ultrasonic probe housing 100 may have an air inlet and an air outlet through which air respectively flows in and out at a position where the heat sink 80 is disposed in order to facilitate a smooth operation of the heat dissipation fan 81.

FIGS. 10, 11, 12, 13, and 14 illustrate various characteristics of an ultrasonic probe, according to another exemplary embodiment.

Figure 10:
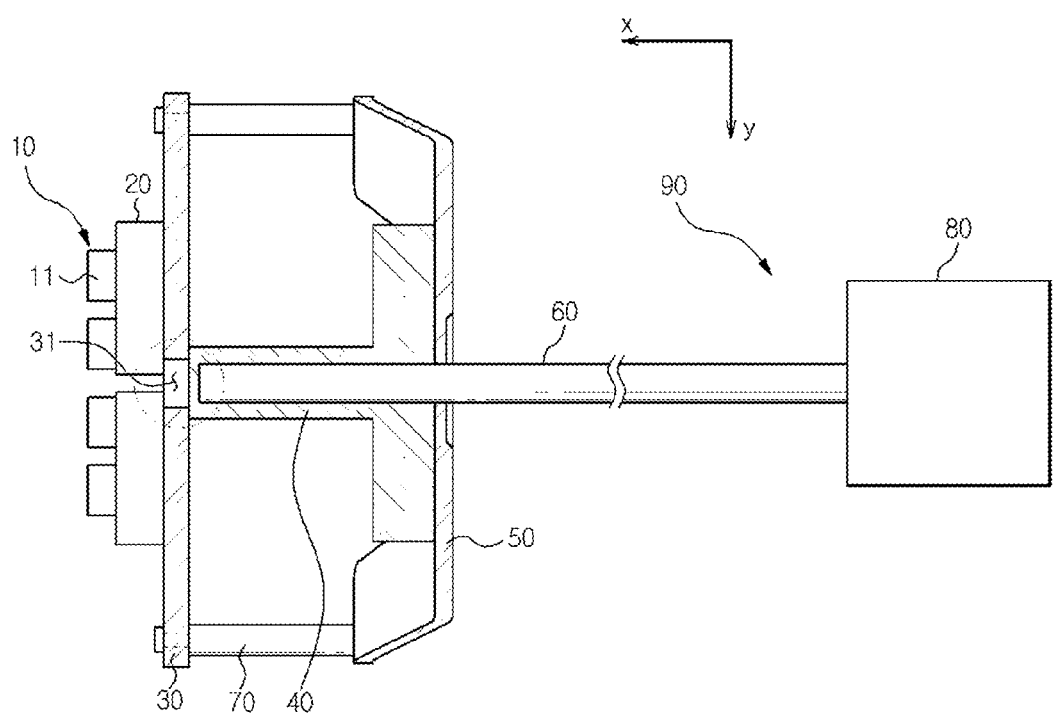
FIG. 10 is a cross-sectional view which illustrates an ultrasonic probe, according to another exemplary embodiment.
Figure 11:
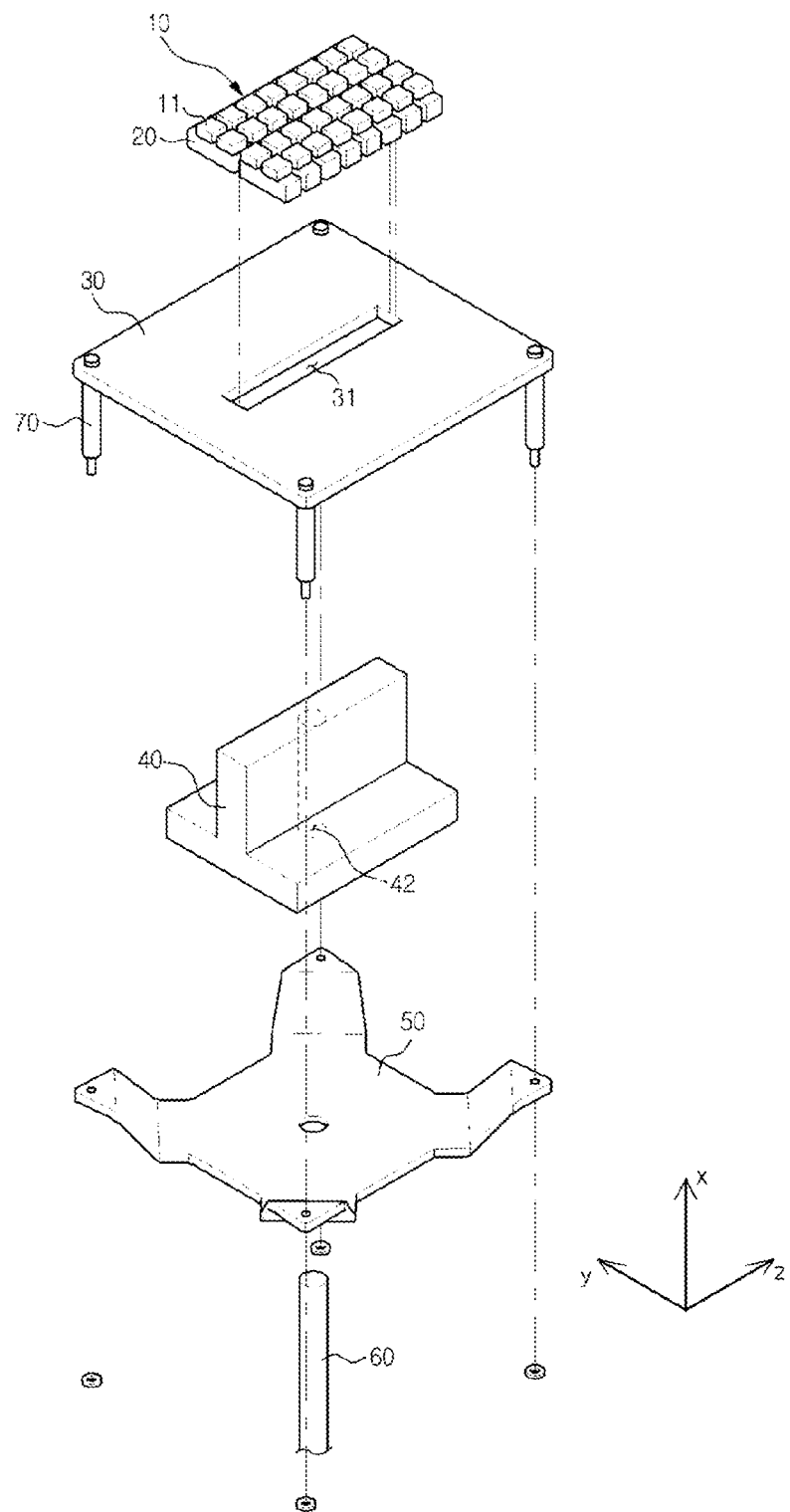
FIG. 11 is an exploded perspective view which illustrates an ultrasonic probe, according to another exemplary embodiment.
Figure 12:
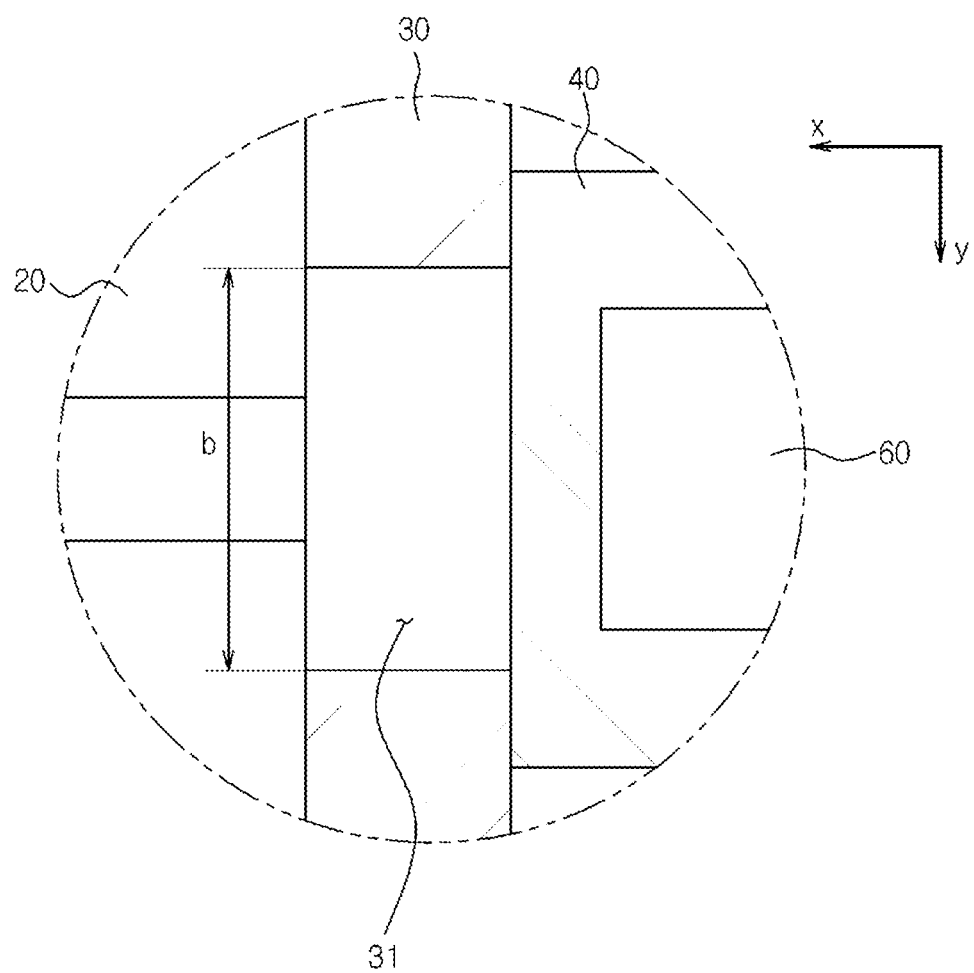
FIG. 12 is a partially enlarged view of FIG. 10.
Figure 13:
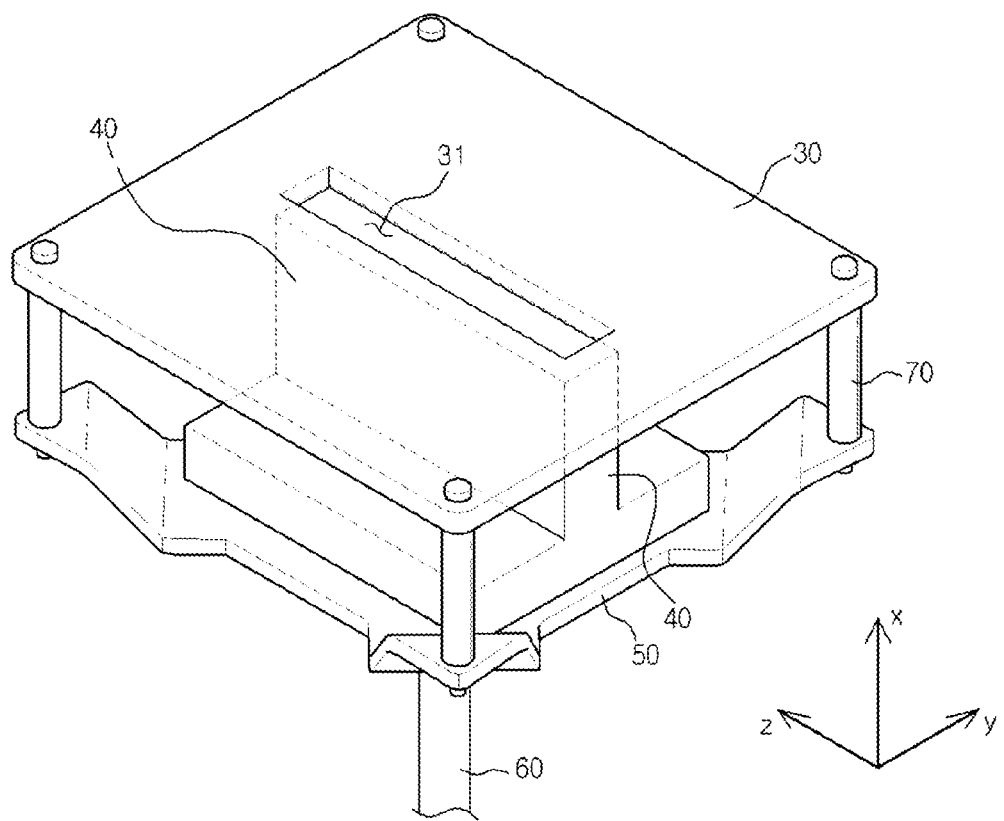
FIG. 13 is a perspective view which illustrates an ultrasonic probe, according to another exemplary embodiment.
Figure 14:
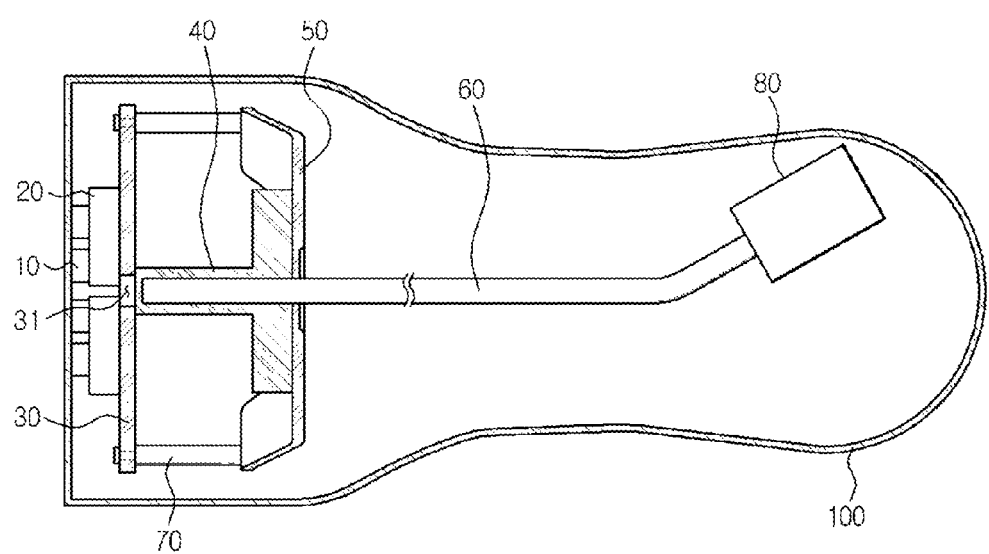
FIG. 14 is a schematic diagram which illustrates the ultrasonic probe of FIG. 10 disposed in a housing.

FIG. 10 is a cross-sectional view which illustrates an ultrasonic probe, according to another exemplary embodiment. FIG. 11 is an exploded perspective view which illustrates an ultrasonic probe, according to another exemplary embodiment of the present invention. FIG. 12 illustrates an enlarged connection structure between a heat spreader 40 and an opening 31 shown in FIG. 10.

The ultrasonic probe according to the present exemplary embodiment includes a heat spreader 40 which absorbs heat which is generated in the integrated circuit 20 in order to facilitate an efficient dissipation of heat which is generated in the integrated circuit 20 to the outside of the ultrasonic probe.

In order to efficiently transfer heat which is generated in the integrated circuit 20 in a situation in which heat is mainly generated to the heat spreader 40, a printed circuit board 30 of the ultrasonic probe has an opening 31 which enables an establishment of a thermal contact between the heat spreader 40 and the integrated circuit 20, as shown in FIGS. 10 to 14.

In particular, as shown in FIG. 11, the printed circuit board 30, which is bonded to the rear surface of the integrated circuit 20, has the opening 31 such that the rear surface of the integrated circuit 20 is partially exposed. According to the present exemplary embodiment, a protrusion, which is inserted into the opening 31 similarly as described above with respect to a previous exemplary embodiment, is not formed on the heat spreader 40.

Further, a width of a front portion of the heat spreader 40 in the y-axis direction may be greater than a length of the opening 31 of the printed circuit board 30 in the y-axis direction, such that the front portion of the heat spreader 40 is not inserted into the opening 31, but instead contacts the rear entrance of the opening 31.

In this structure, a gap is provided between the rear surface of the portion of the integrated circuit 20 which is exposed via the opening 31 and the front portion of the heat spreader 40 by a depth of the opening 31.

The gap may be filled with a thermal medium which has a relatively high thermal conductivity, such as, for example, a thermal grease or a phase change material, in order to facilitate an efficient transfer of heat which is generated in the integrated circuit 20 to the heat spreader 40.

When the gap is filled with the thermal medium which has the relatively high thermal conductivity, the heat spreader 40 thermally contacts the rear surface of the integrated circuit 20 via the thermal grease or the phase change material, which acts as a medium.

The other components are the same or similar as corresponding components which are described above, and thus detailed description thereof will be omitted.

Although a few exemplary embodiments have been shown and described, it will be appreciated by those skilled in the art that changes may be made in these exemplary embodiments without departing from the principles and spirit of the present inventive concept, the scope of which is defined in the claims and their equivalents.

What is claimed is:

1. An ultrasonic probe comprising:
 a transducer which is configured to generate ultrasound irradiation;
 an integrated circuit which is installed on a rear surface of the transducer;
 a printed circuit board which is installed on a rear surface of the integrated circuit and includes an opening via which the rear surface of the integrated circuit is at least partially exposed;
 a heat spreader which includes a protrusion inserted into the opening of the printed circuit board, and which is configured to absorb heat generated in the integrated circuit; and a heat dissipation module which is configured to release heat absorbed by the heat spreader to an outside,
wherein the heat dissipation module comprises:
a heat pipe which is configured to transfer heat absorbed by the heat spreader in a direction opposite to an ultrasound irradiation direction; and
a heat sink which is configured to release heat transferred by the heat pipe to the outside.

2. The ultrasonic probe according to claim 1, wherein a gap is provided between the protrusion of the heat spreader and the integrated circuit.

3. The ultrasonic probe according to claim 2, wherein the gap is filled with at least one of a thermal grease and a phase change material.

4. The ultrasonic probe according to claim 1, wherein the heat spreader comprises an insertion groove into which the heat pipe is insertable, and wherein the heat pipe is inserted into the insertion groove.

5. The ultrasonic probe according to claim 4, wherein the insertion groove extends from the rear surface of the heat spreader toward the protrusion.

6. The ultrasonic probe according to claim 1, wherein the heat sink comprises:
a heat dissipation plate which is configured to disperse heat transferred by the heat pipe; and
a heat dissipation fan which is configured to release heat dispersed by the heat dissipation plate to the outside.

7. The ultrasonic probe according to claim 1, wherein a fixing plate is installed on a rear surface of the heat spreader, and wherein a coupling member connects the fixing plate to the printed circuit board such that the heat spreader is fixed to the printed circuit board.

8. The ultrasonic probe according to claim 1, wherein the transducer includes a capacitive micromachined ultrasonic transducer (cMUT).

9. An ultrasonic probe comprising:
a transducer which is configured to generate ultrasound irradiation;
an integrated circuit which is installed on a rear surface of the transducer;
a printed circuit board which is installed on a rear surface of the integrated circuit and includes an opening via which the rear surface of the integrated circuit is at least partially exposed; and
a heat spreader which is configured to absorb heat generated in the integrated circuit via the opening of the printed circuit board.

10. The ultrasonic probe according to claim 9, wherein the heat spreader is installed on a rear surface of the printed circuit board, and a space between a portion of the rear surface of the integrated circuit which is exposed via the opening and a portion of a front surface of the heat spreader which corresponds to the opening is filled with a thermal medium.

11. The ultrasonic probe according to claim 10, wherein the thermal medium comprises at least one of a thermal grease and a phase change material.

12. The ultrasonic probe according to claim 9, wherein a fixing plate is installed on a rear surface of the heat spreader, and wherein a coupling member connects the fixing plate to the printed circuit board such that the heat spreader is fixed to the printed circuit board.

13. The ultrasonic probe according to claim 9, further comprising:
a heat pipe which is configured to transfer heat absorbed by the heat spreader in a direction opposite to an ultrasound irradiation direction; and
a heat sink which is configured to release heat transferred by the heat pipe to an outside.

14. The ultrasonic probe according to claim 13, wherein the heat spreader comprises an insertion groove into which the heat pipe is insertable, and wherein the heat pipe is inserted into the insertion groove.

15. The ultrasonic probe according to claim 13, wherein the heat sink comprises:
a heat dissipation plate which is configured to disperse heat transferred by the heat pipe; and
a heat dissipation fan which is configured to release heat dispersed by the heat dissipation plate to the outside.

16. An ultrasonic probe comprising:
a transducer which is configured to generate ultrasound irradiation;
an integrated circuit which is installed on a rear surface of the transducer;
a printed circuit board which is installed on a rear surface of the integrated circuit and includes an opening via which the rear surface of the integrated circuit is at least partially exposed;
a heat spreader which is disposed at a rear surface of the printed circuit board and includes a protrusion inserted into the opening of the printed circuit board, and is configured to absorb heat generated in the integrated circuit;
a heat pipe which is configured to transfer heat absorbed by the heat spreader in a direction which is opposite to an ultrasound irradiation direction; and
a heat sink which is configured to release heat transferred by the heat pipe to an outside,
wherein the heat spreader comprises an insertion groove into which the heat pipe is inserted, and a gap is provided between the protrusion of the heat spreader and the integrated circuit.

* * * * *